United States Patent [19]

Brady et al.

[11] 3,931,341

[45] Jan. 6, 1976

[54] TREATED PENTACHLOROPHENOL

[75] Inventors: Thomas P. Brady, Natick; Horst G. Langer, Wayland, both of Mass.

[73] Assignee: The Dow Chemical Company, Midland, Mich.

[22] Filed: Apr. 16, 1973

[21] Appl. No.: 351,229

[52] U.S. Cl............ 260/623; 117/100 R; 117/100 A; 260/621 R; 424/353
[51] Int. Cl.[2]............................................ C07c 39/36
[58] Field of Search ........ 260/623 R, 619 R, 621 R; 117/100 R, 100 A; 424/353

[56] References Cited
UNITED STATES PATENTS

| | | | |
|---|---|---|---|
| 3,231,640 | 1/1966 | Kloft | 260/623 R |
| 3,646,225 | 2/1972 | Morrison | 260/623 R |
| 3,692,561 | 9/1972 | Hager | 260/623 R |

*Primary Examiner*—James O. Thomas, Jr.
*Assistant Examiner*—W. B. Lone
*Attorney, Agent, or Firm*—A. R. Whale

[57] ABSTRACT

Free flowing particulate pentachlorophenol having little or no tendency to bloom is obtained by incorporating about 0.5–10 percent by weight of benzyl alcohol. Prills made from molten pentachlorophenol containing the benzyl alcohol are a preferred form.

2 Claims, No Drawings

TREATED PENTACHLOROPHENOL

BACKGROUND OF THE INVENTION

This invention relates to a method of treating pentachlorophenol to reduce its tendency to bloom or sublime and to the treated pentachlorophenol thereby obtained.

Pentachlorophenol is a well known fungicide and preservative which is widely used to preserve wood, particularly that which is exposed to the soil or other sources of moisture. Pentachlorophenol is sold in bulk as a granular solid, either flakes or prills. The solid material, particularly when freshly prepared, has a strong tendency to bloom or sublime whereby very fine crystals form on the surface. This coating of crystals is easily dislodged during handling and opening a container can release a cloud of dust which is intensely irritating to eyes, nose, and throat.

Pentachlorophenol has been treated in a number of ways to avoid this problem. The granular material has been tumbled in hot air to make a product having a smooth surface and less tendency to bloom (Canadian Pat. No. 749,423). It has been treated with diethanolamine or triethanolamine to reduce dusting and residual acid (U.S. Pat. No. 3,646,225). Oil treatments have long been used for dusty solids and pentachlorophenol has been given a dual treatment with oil and a glycol to reduce dusting (U.S. Pat. No. 3,692,561). All of these treatments are effective to some degree, but most have economic or other disadvantages. The effect of some is of short duration and blooming may start a few days or weeks after the treatment. Hot air treatment may increase the formation of insoluble sludges upon dissolving the treated pentachlorophenol in a solvent to treat wood. Oil tends to darken the treated pentachlorophenol and it may cause staining or deterioration of the container.

SUMMARY OF THE INVENTION

It has now been found that blooming of solid pentachlorophenol is substantially reduced or eliminated by incorporating in the pentachlorophenol about 0.5–10 percent by weight of benzyl alcohol. The treatment is effective in any solid form of pentachlorophenol whether flakes or prills and the granular material remains essentially unchanged in appearance and free flowing even after prolonged storage.

DETAILED DESCRIPTION

The benzyl alcohol can be applied to particulate pentachlorophenol as a coating by spraying the liquid alcohol or a solution of the alcohol in a volatile solvent over the solid material. Solid beads or prills can also be tumbled in the presence of the liquid alcohol or solution of the alcohol to obtain the same result. Alternatively, the benzyl alcohol can be added to molten pentachlorophenol to form a uniform mixture prior to a flaking or prilling operation. Essentially equivalent results are obtained by all of these methods, but the latter method generally gives more uniform results and is preferred. Preferred concentrations are in the range of 1–5 percent. Less than 0.5 percent provides insufficient coating of the pentachlorophenol and some blooming may result while more than ten percent of benzyl alcohol tends to make the treated material slightly sticky so that it may cake during storage.

This invention provides a simple and effective procedure using a single inert additive in relatively small amount to eliminate or substantially reduce blooming of pentachlorophenol without significantly altering the appearance and other characteristics of the solid material. The treated solid is more easily handled, it can be stored for extensive periods without any substantial change, it remains completely free flowing, and its fungicidal and preservative efficiency is essentially undiluted.

EXAMPLES 1-3

Benzyl alcohol was added to pentachlorophenol in different concentrations and by different methods to obtain free flowing, nonblooming products. In one experiment, 5 percent by weight benzyl alcohol was added to molten pentachlorophenol and the liquid mixture was then converted into beads about 1–1.5 mm. in diameter by a standard prilling procedure. Two samples of untreated pentachlorophenol prills were uniformly wet with chloroform solutions of benzyl alcohol and the chloroform was evaporated off to make prills containing 8 and 10 percent benzyl alcohol respectively. These three samples were stored at room temperature in closed containers for 6 months. All remained free flowing and showed no signs of blooming. Untreated prills under the same conditions developed a considerable surface growth of fine needle-like crystals.

We claim:
1. Substantially free flowing, non-blooming pentachlorophenol having admixed therewith about 0.5–10% by weight of benzyl alcohol.
2. The composition of claim 1 wherein about 1–5 percent of benzyl alcohol is present.

* * * * *